United States Patent [19]
Muriot

[11] 3,963,027
[45] June 15, 1976

[54] MEDICAL/SURGICAL SUCTION EQUIPMENT

[75] Inventor: Edward E. Muriot, Horsham, Pa.

[73] Assignee: Health Technology Labs, Inc., Horsham, Pa.

[22] Filed: Nov. 15, 1974

[21] Appl. No.: 524,052

Related U.S. Application Data

[63] Continuation-in-part of Ser. No. 497,838, Aug. 16, 1974, abandoned.

[52] U.S. Cl. .......................... 128/276; 128/DIG. 24
[51] Int. Cl.² .......................................... A61M 1/00
[58] Field of Search .......................... 128/276–278, 128/297–300, DIG. 24; 16/2; 277/178; 220/9, DIG. 9; 312/296; 285/192

[56] References Cited
UNITED STATES PATENTS

| | | | |
|---|---|---|---|
| 1,697,814 | 1/1929 | Forbes | 277/178 |
| 2,757,669 | 8/1956 | Gewecke et al. | 128/276 |
| 2,897,533 | 8/1959 | Bull et al. | 277/178 |
| 3,142,298 | 7/1964 | Koski et al. | 128/276 |
| 3,552,754 | 1/1971 | Bow | 16/2 |
| 3,599,639 | 8/1971 | Spotz | 128/276 |
| 3,640,276 | 2/1972 | Dancy, Jr. | 128/214 F |
| 3,773,211 | 11/1973 | Bridgman | 128/276 |
| 3,774,613 | 11/1973 | Wood, Jr. et al. | 128/277 |
| 3,780,738 | 12/1973 | Deaton | 128/277 |

FOREIGN PATENTS OR APPLICATIONS

| | | | |
|---|---|---|---|
| 2,127,764 | 7/1971 | Germany | 128/276 |

Primary Examiner—Robert W. Michell
Assistant Examiner—Henry S. Layton
Attorney, Agent, or Firm—Synnestvedt & Lechner

[57] ABSTRACT

Equipment for medical or surgical uses is provided for purposes, for example, of withdrawing or draining body liquids from cavities tending to accumulate such liquids, for instance as a result of wounds, surgical procedures or of pathological conditions in the body. The equipment comprises a vacuum chamber adapted to receive a disposable collection bag, having a suction line with a catheter for receiving the body liquids, together with control systems for regulating the vacuum in the vacuum chamber and thus the suction in the collection bag.

12 Claims, 17 Drawing Figures

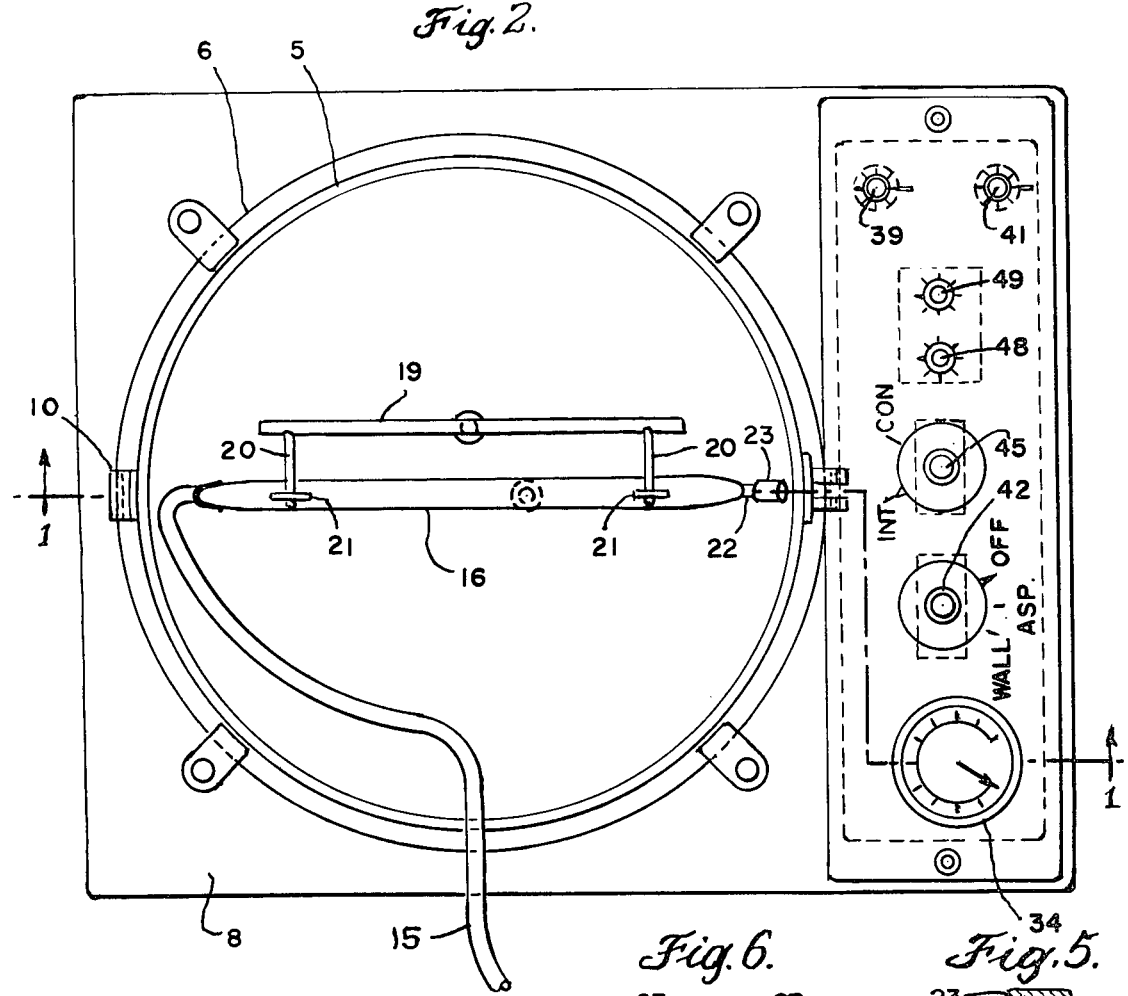
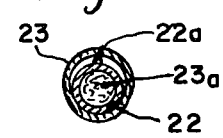
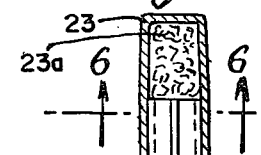
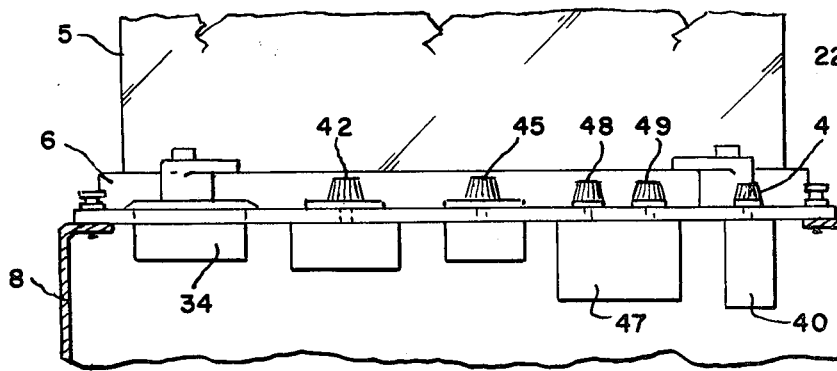

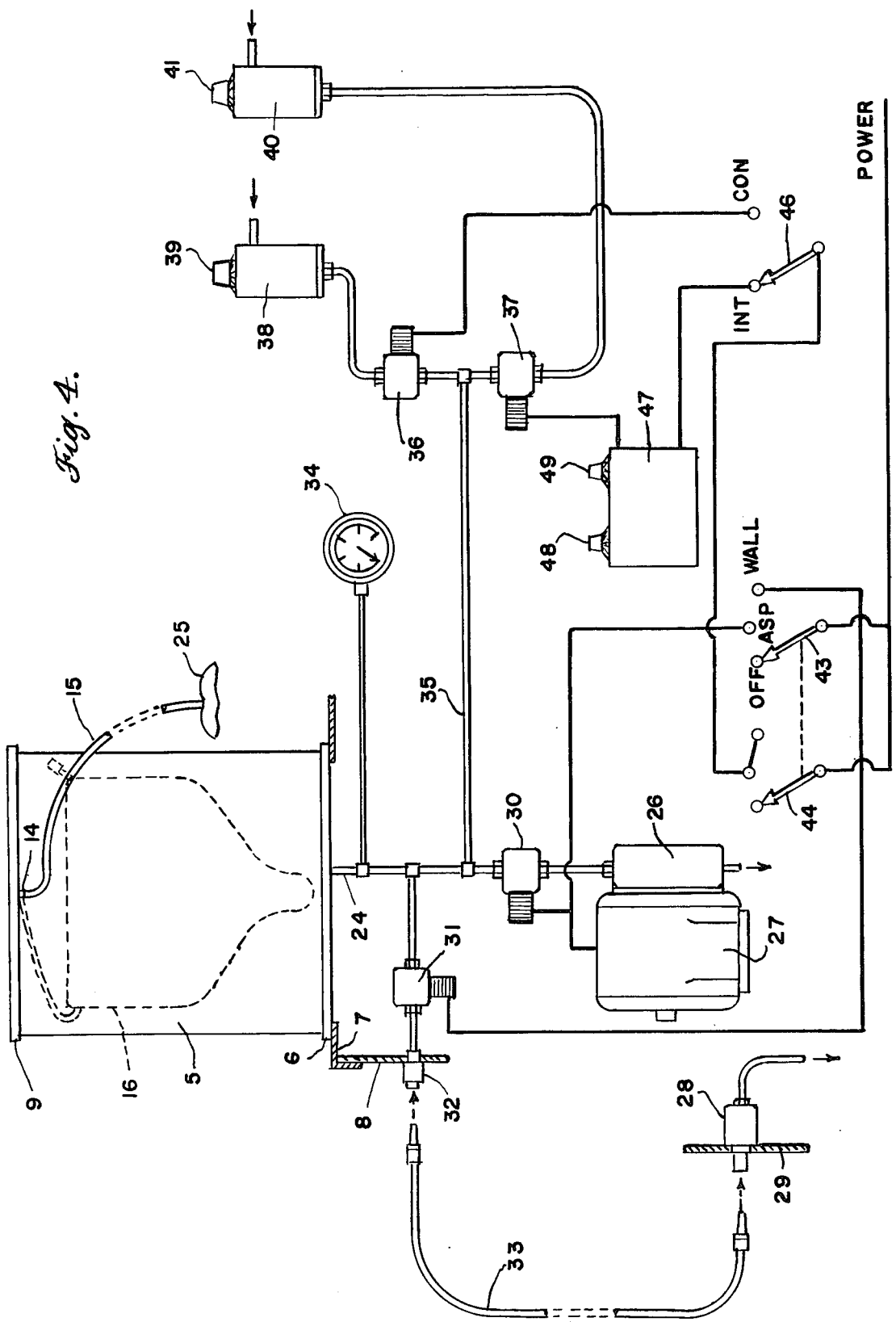

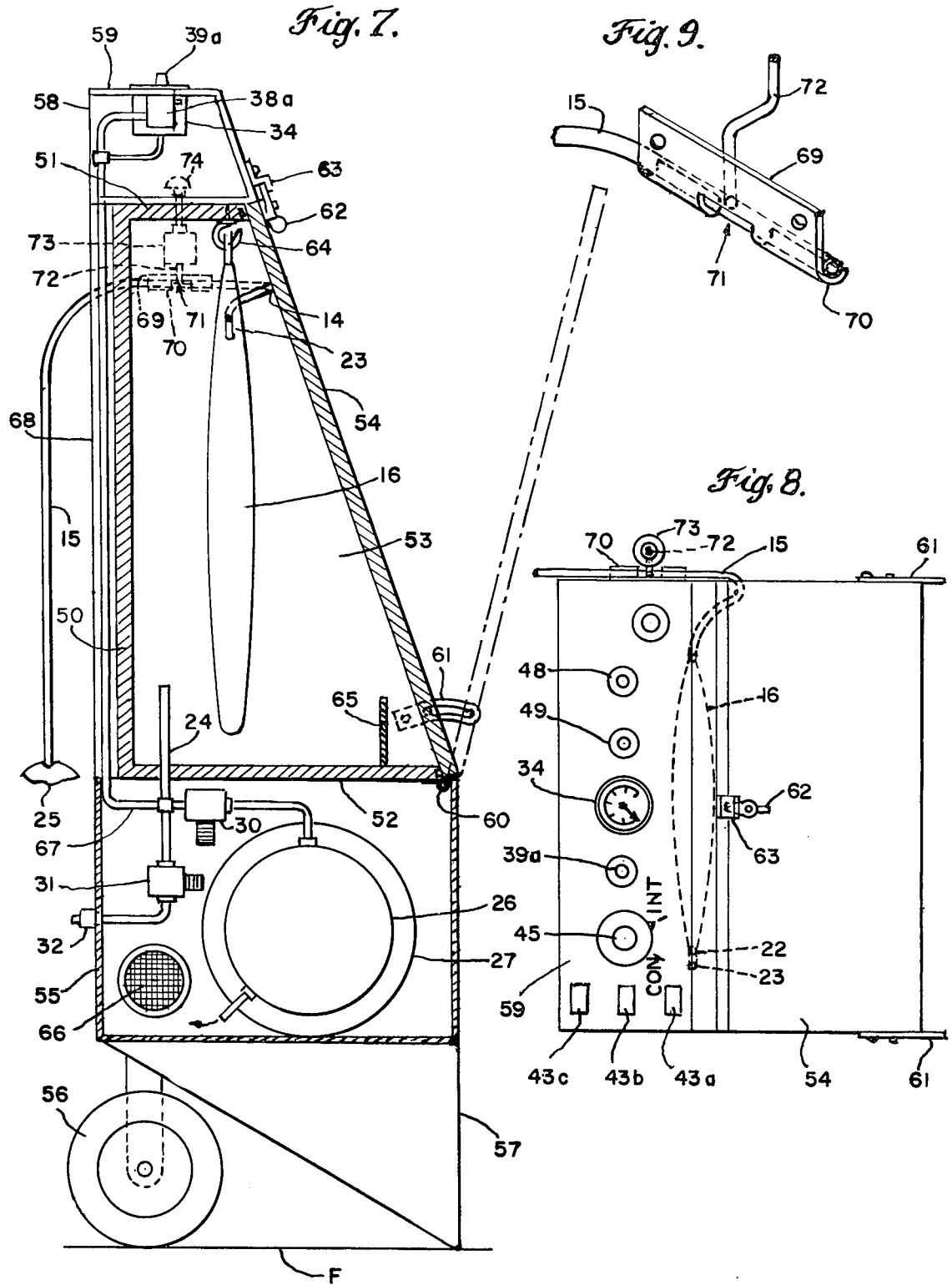

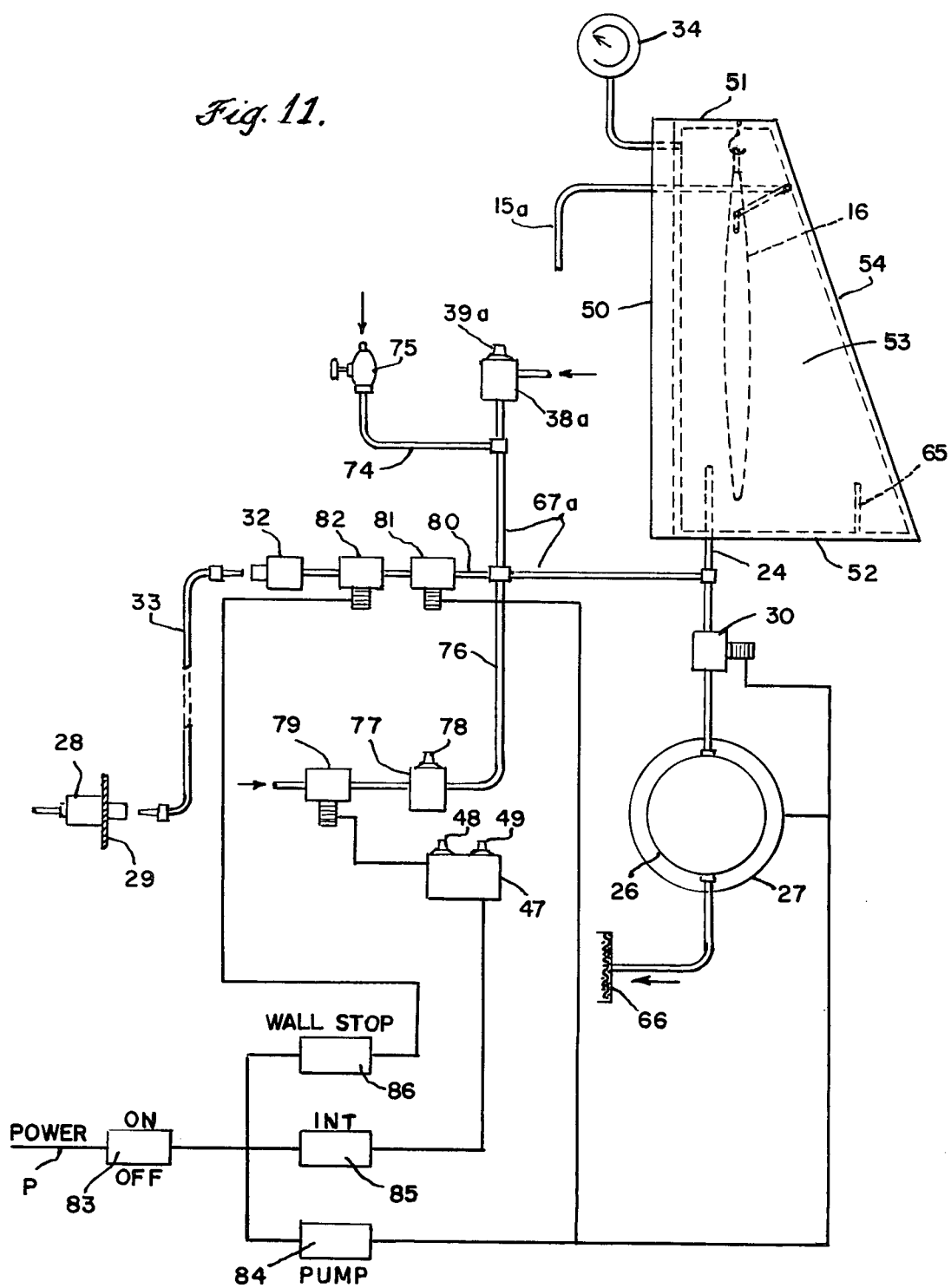

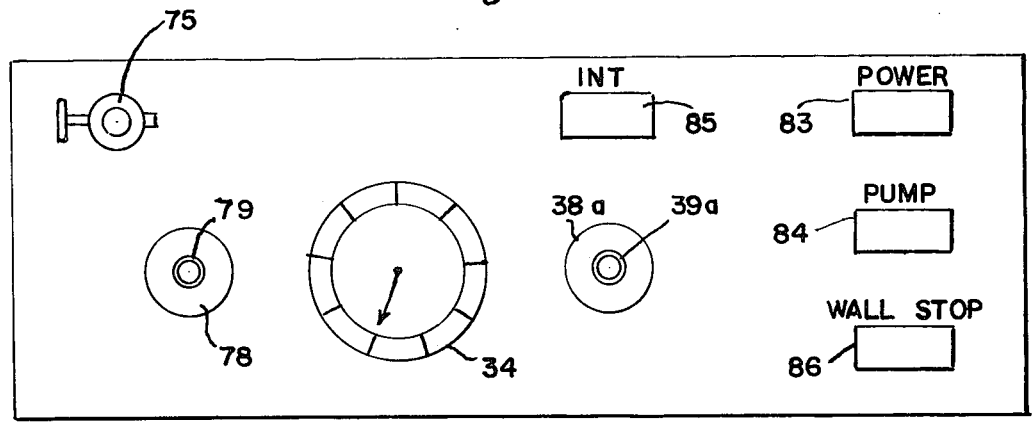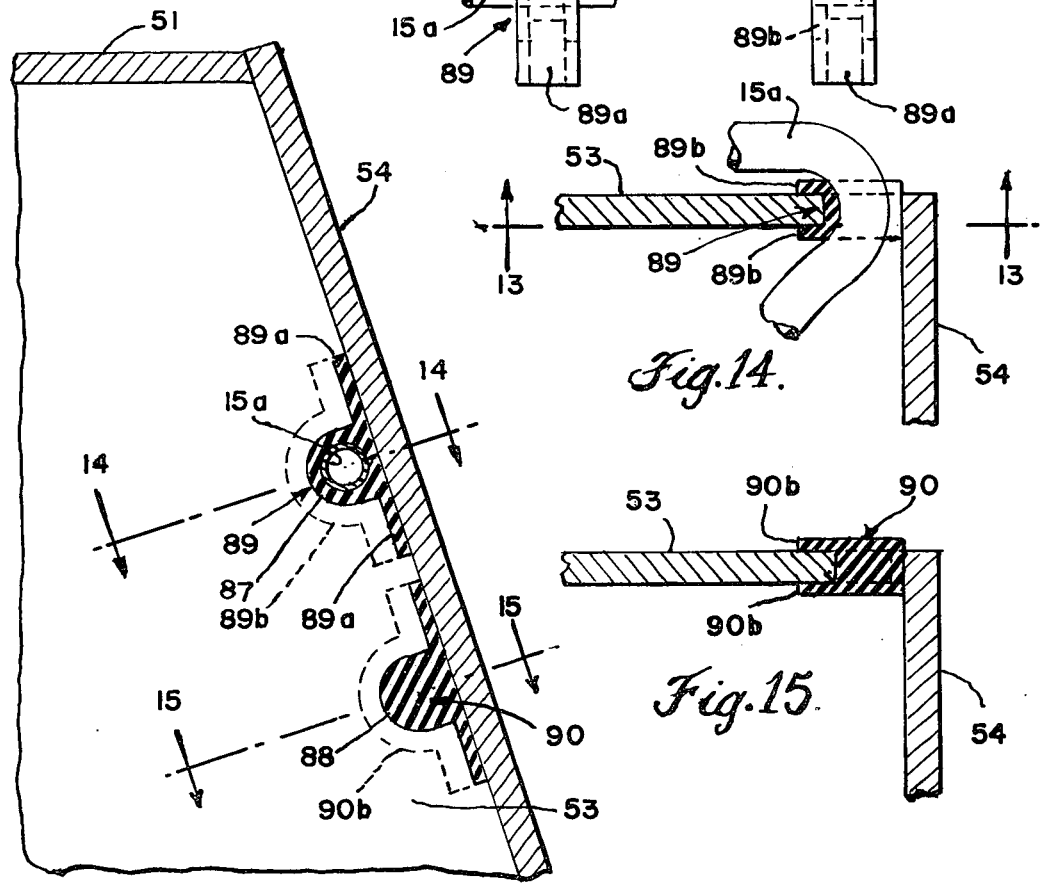

MEDICAL/SURGICAL SUCTION EQUIPMENT

This application is a Continuation-in-part of my application Ser. No. 497,838, filed Aug. 16, 1974, now abandoned.

The present invention relates to suction equipment for use for medical or surgical purposes, and particularly for the purpose of withdrawing from the body liquids tending to accumulate in cavities or regions of the body because of disease or malfunction or other pathological conditions, or because of surgical or medical procedures. Such conditions at times may also tend to accumulate solids, and it will be understood that the equipment of the invention may also serve to withdraw such solids in suspension in liquids being withdrawn.

One of the principal objectives of the present invention is to provide equipment of the type referred to which is arranged to function on the vacuum or suction principle, without the flow of the liquids through a mechanical pump or pumping mechanism, as has been the case in certain prior arrangements.

A further object of the invention is to provide a high degree of flexibility in the control of the suction, both with respect to the amount of suction applied, and also with respect to the timing thereof. Thus, according to the invention, provision is made not only for adjustment for the amount of vacuum or suction, but also for alternative conditions of operation in which the suction may either be applied continuously, or may be applied intermittently, or may be applied in a manner providing intermittent fluctuation of the suction between high and low suction values.

Still further, it is an object of the invention to provide for operation of the equipment intermittently, with provision for regulation of the duration of the suction intervals as well as for the duration of the "pauses" between the periods when suction is applied.

In accordance with another aspect of the invention, the equipment includes a vacuum chamber adapted to receive an expandable and disposable suction bag having a catheter extended therefrom through the wall of the vacuum chamber so that it may be placed in the wound or other cavity from which drainage is desired.

It is also an object of the invention to provide alternatively for insertion of one or more than one bag in the vacuum chamber, each such bag having an intake tube with a catheter for receiving liquids either from the same or from different sources.

It is an object of the invention to provide an exceedingly simple and effective system for replacing the disposable bag and catheter, notwithstanding the normal enclosure thereof in the vacuum chamber.

In one embodiment of the invention intermittent operation is achieved by alternately interrupting and reestablishing the vacuum in the vacuum chamber.

In a second embodiment intermittent operation is achieved by alternately closing and opening the suction line extended from the collection bag to the intake catheter. In the second embodiment it is an objective to provide for intermittent operation without changing the pressure in the vacuum chamber and also without risk of any backflow in the suction line extended from the suction bag to the intake catheter.

In a third embodiment intermittent operation is achieved by intermittent fluctuation of the suction between high and low suction levels. As in the second embodiment it is an objective of this third embodiment to eliminate risk of backflow in the suction line extended from the bag to the intake catheter.

It is another object of the invention to provide sealing means for the suction tube of the bag at the point where the suction tube extends through the wall of the vacuum chamber and it is contemplated according to the invention that sealing means or devices be provided to accommodate suction tubes of different sizes.

Still another object of the invention is to provide sealing means, of the kind just referred to, in the form of an adaptor which is preferably permanently fastened to the suction tube, thereby avoiding inadvertent use of adaptors of the wrong size by personnel operating the equipment.

Still another object of the invention is to provide suction equipment of the kind above mentioned adapted alternatively to operate either upon a self-contained suction source, or upon an external suction source, such as commonly provided in hospital rooms, and in which provision is made for automatic change over from operation on the self-contained suction source to operation on the external suction source, in the event of failure of the power operating the self-contained suction source.

How the foregoing and other objects and advantages are attained will appear more fully from the following description referring to the accompanying drawings, in which:

FIG. 2 is a plan view, with the top cover of the vacuum chamber removed, taken as indicated by the line 2—2 on FIG. 1;

FIG. 3 is a fragmentary view taken from the right of FIG. 2 and illustrating the location and arrangement of the controls and certain other parts;

FIG. 4 is a schematic view of the fluid pressure controls and control system for the equipment of the first embodiment, and also certain electrical controls associated therewith;

FIG. 5 is a fragmentary axial sectional view of the outlet tube of the bag;

FIG. 6 is a cross sectional view taken as indicated by the section line 6—6 on FIG. 5;

FIG. 7 is a vertical sectional view of an alternative embodiment of the suction equipment of the present invention;

FIG. 8 is a plan view of the equipment shown in FIG. 7;

FIG. 9 is an enlarged isometric fragmentary view of a device used for establishing intermittent operation in the embodiment of FIGS. 7 and 8;

FIG. 11 is a schematic view of the general type of FIG. 10 but illustrating certain parts of a third embodiment of the equipment and controls;

FIG. 12 is a view of a control panel contemplated for use with the controls shown in FIG. 11;

FIG. 13 is an enlarged view of certain details of construction of the third embodiment and particularly showing sealing means for use with the suction tubes, this view being taken as indicated by the section line 13—13 on FIG. 14;

FIGS. 14 and 15 are fragmentary sectional views taken as indicated by the section lines 14—14 and 15—15 on FIG. 13; and FIGS. 16 and 17 are views illustrating certain details of tube sealing devices.

Figure 1:
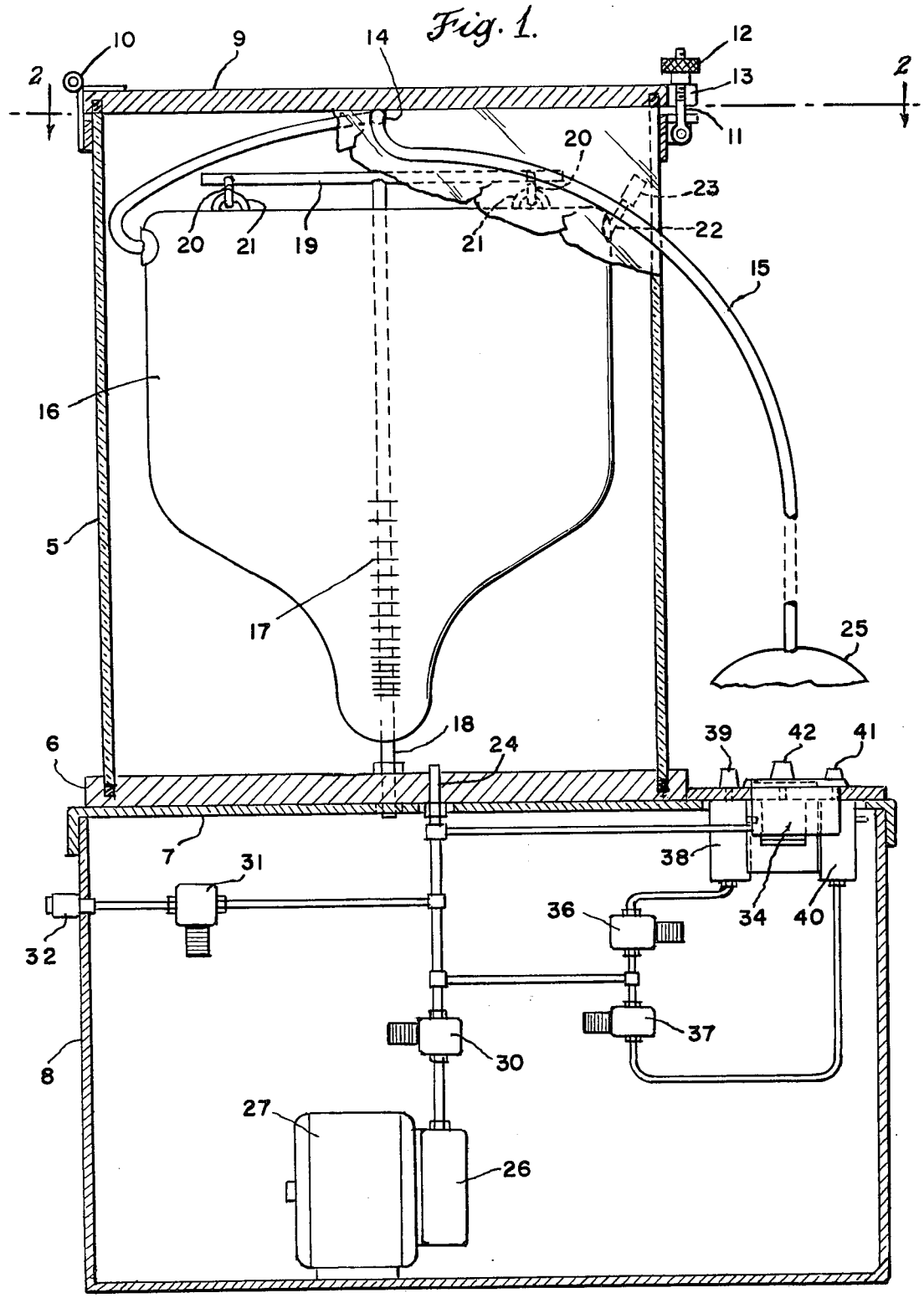
FIG. 1 is an elevational view, mostly in vertical section, of the physical arrangement of the major components of a first embodiment of equipment constructed according to the present invention, taken as indicated by the line 1—1 on FIG. 2.

Referring first to the first embodiment as shown in FIGS. 1, 2 and 3, a vacuum chamber is provided, being formed by a cylindrical body 5, preferably made of transparent material, such as polymethyl methacrylate, but it is to be understood the main body of the chamber may be constructed in various different ways. The cylindrical body 5 has its lower edge sealed in a groove provided in the base plate 6, which is mounted on the top deck 7 of a base or cabinet 8 in which some of the controls and other equipment are housed. These major components of the system are preferably arranged as a portable unit which may be taken to any desired point of use.

At the top of the cylindrical body 5 there is a removable or separable closure plate 9, which is also desirably formed of transparent plastic material and which is hinged to the cylindrical body 5 as indicated at 10 and which further has a separable fastener such as the swing bolt 11 provided with a knurled nut 12, the bolt 11 being accommodated in a recess 13 formed in the edge of the lid 9.

The upper edge of the cylindrical body 5 is also provided with a notch or recess 14 to accommodate the suction tube 15 which is connected with the suction bag 16 arranged within the vacuum chamber. Suction bag 16 with the tube 15 desirably constitutes a disposable unit. These parts are desirably formed of flexible plastic material, preferably transparent or at least translucent so that the quantity of liquid in the bag may be observed and the bag may have a series of graduations 17 from which a reading may be taken of the volume of liquids contained in the bag.

The various parts of the vacuum chamber are sealed to each other in order to prevent loss of vacuum, and the notch 14 for the tube 15 should fit snugly, preferably with a sealing element therebetween.

The bag has a suction tube 15 which may terminate in or be provided with a disposable catheter for insertion into the zone or cavity from which the liquids are to be withdrawn. The bag also has a drain spout 22 with a cap 23 connected with the bag in an upper portion thereof above the normal level to which the bag is filled. The details of construction of the spout and cap appear in FIGS. 5 and 6. Tube 22 has a longitudinal rib 22a, so that when the cap 23 is applied there remain small leakage passages at each side of the rib 22a. This provides for communication of the vacuum in the chamber into the interior of the bag, so that the actual transfer of the liquids is effected under the influence of atmospheric or other pressure upon the liquids in the region of the catheter, which pressure, and the reduced pressure established in the bag by the vacuum provides the pressure differential which is effective to transfer the liquids from the zone being drained into the bag. A wad of cotton or other similar material 23a in the cap 23 acts as a filter preventing transfer of liquid or contaminants from the bag into the surrounding vacuum chamber. If desired the cap may be removed to permit use of the spout 22 as a drainage tube for emptying the bag, for purposes of analysis, test or disposal.

The bag may be supported within the vacuum chamber by various supporting devices preferably cooperating with the top portion of the bag, as by a standard 18 having a cross bar 19 at the top with a pair of hooks 20 adapted to be received in the loops 21 provided at the top edge of the bag. With the bag suspended at the top as just described and with the closure 9 displaceable upwardly about the hinge 10 and still further with the notch 14 in the upper edge of the cylindrical body 5 for receiving the tube 15, the insertion and replacement of the disposable bags is exceedingly simple and may be effected with minimum effort and time.

The suspension of the bag at the top, as shown, and the connection of the suction tube 15 with the upper region of the bag is also advantageous because this arrangement avoids interference with or alteration of the suction as a result of build up of the body of liquid within the bag. If the suction tube 15 were connected with the bottom or in the bottom region of the bag, the gravity head of the accumulating liquid would interfere with and reduce the suction action, and this is avoided by arranging the suction connection so that it communicates with the suction bag in the upper portion thereof, and in any event above the level to which it is intended that the liquid would be permitted to rise in the bag.

As above mentioned, the base or cabinet 8 houses various parts of the controls and control system and the pressure reduction within the vacuum chamber 5 is effected through a vacuum connection 24, preferably arranged in the bottom of the chamber and extended therefrom downwardly for association with the control system housed within the base 8. The various parts of the control system are hereinafter described first with reference to FIG. 4 where the control system is illustrated schematically. In FIG. 4 the vacuum chamber and the suction bag are also indicated somewhat diagrammatically, and in both FIGS. 1 and 4 the suction tube 15 is indicated as having its catheter or free end associated with a portion of a body, diagrammatically indicated at 25, from which it is desired to withdraw liquids.

In the preferred embodiment of the equipment, it is contemplated that the pressure reduction may be effected as a result of association of the vacuum connection 24 with either one of two pressure reduction sources. One of these comprises a self-contained suction or aspirator pump indicated at 26, driven by a motor 27 and housed within the base 8 of the equipment. Alternatively, it is contemplated that the vacuum connection 24 may be coupled with a so-called "vacuum outlet" which is commonly available in hospital rooms as a "plug in" vacuum connection coupling, usually provided on the wall near the head end of the hospital bed. Such a coupling is indicated at 28 in FIG. 4, provided in the wall 29 of the hospital room.

It is customary in this type of vacuum outlet that the vacuum connection is automatically open or established when the coupling element is inserted in the wall connection.

The first of these two sources of vacuum (the pump 26) is coupled with the connection 24 through a normally closed solenoid operated valve 30. The second of these two sources is adapted to be coupled with the vacuum connection 24 through another normally closed solenoid operated valve 31 which, in turn, is connected with a coupler 32 provided in the wall of the base 8. A removable length of tubing 33 having separable couplers at both ends serves to connect the wall outlet 28 with the coupling 32, and thereby provide for completion of the flow path from the vacuum connection 24 to the vacuum wall outlet 28.

A pressure gauge 34 is associated with the connection 24 in order to provide a reading of the pressure level or vacuum established within the vacuum chamber 5.

Tubing 35 is extended from the vacuum connection 24 to a pair of additional normally closed solenoid actuated valves 36 and 37. The valve 36 has associated therewith a bleed valve 38 adjustable by means of a knob 39. Similarly, the valve 37 has associated therewith a bleed valve 40 adjustable by means of a knob 41. These two bleed valves are respectively effective when the valves 36 and 37 are opened to provide for regulation of the vacuum, i.e., of the extent of pressure reduction in the chamber 5. It will be understood that in general, the sources of press-ure reduction 26 and 28 represent substantially constant press-ure reduction sources of relatively high value, so that if the pressure reduction from either of these sources is communicated to the vacuum chamber, without some reduction, for most purposes the vacuum and suction developed would be higher than that desired. Therefore, one or the other of the adjustable bleed valves 38 or 40 is employed to bleed air at atmospheric pressure into the system and thereby diminish the extent of pressure reduction or vacuum which will be developed in the vacuum chamber 5.

The control by which an operator may select which of the two pressure reduction sources (26 or 28) is to be employ-ed constitutes a switch in an electrical control circuit which is indicated in FIG. 4 purely diagrammatically. This control switch comprises a control knob 42 (see FIGS. 2 and 3) having two gauged switch levers 43 and 44 (see FIG. 4). The switch lever 43 controls the solenoid operated valves 30 and 31, having three positions, namely OFF, ASP, and WALL. In the OFF position both of the valves 30 and 31 remain closed and the vacuum system is out of service. In the ASP position the valve 30 is opened and the motor 27 is operating so that the pressure reduction is derived from the internally located aspirator pump 26. In the WALL position the valve 31 is opened and the pressure reduction is derived from the wall outlet 28.

It will be noted that in either the ASP or WALL position, the ganged second switch lever 44 provides for delivery of power to another switch having a knob 45 (see FIGS. 2 and 3) operating a switch lever 46 which may selectively or alternatively be positioned in the INT or the CON positions, as indicated in FIG. 4. In the CON position the solenoid valve 36 is opened and the bleed valve 38 is effective to regulate the pressure reduction in the chamber 5, and this represents a constant operating condition which may be maintained at any desired pressure level according to the adjustment of the knob 39.

When the switch lever 46 is in the INT position, the valve 37 may be opened, but this opening is effected under the influence of the timer device indicated at 47. The timer has two controls 48 and 49, the first providing for control of the period of time during which the valve 37 is opened, and the second providing for control of the length of the interval between the periods during which the valve 37 is opened. In this way the suction may be made intermittent, as is sometimes desirable in order to provide for withdrawal of body liquids for only short periods of time, at timed intervals. It will be understood that any suitable switches, solenoids, timers and the like may be utilized, such individual components forming no part of the present invention per se.

From the foregoing it will be seen that the equipment of the first embodiment of the invention provides great flexibility in control and in the operating conditions, the extent of pressure reduction being variable at will by the bleed valves 38 and 40, which are respectively operative either in the continuous mode or in the intermittent mode, and this regardless of which of the pressure sources is relied upon to effect pressure reduction in the vacuum chamber.

Turning now to the embodiment illustrated in FIGS. 7–10 inclusive, it is first pointed out that a number of parts and devices employed are the same or essentially the same as those utilized in the first embodiment and described above. The same reference numerals are employed on such parts or components and they will be referred to in the following description only generally, instead of in detail in view of the description previously given.

The embodiment of FIGS. 7–10 incorporates a number of distinctive features as compared with the first embodiment and these distinctive features are emphasized in the following description.

Reference is first made to the overall general configuration of the equipment shown in FIGS. 7–10 and it will be seen that the vacuum chamber of this embodiment is made up of assembled flat sheets or wall elements, at least some of which are preferably formed of transparent plastic or resin material such as polymethyl methacrylate. The vacuum chamber is defined by a back wall 50, top and bottom walls 51 and 52, upright end walls 53, and an inclined front wall 54. At least the front wall 54, which is arranged to serve as a door or closure, as more fully brought out herebelow, is preferably formed of transparent material, and desirably also the side walls. The vacuum chamber is arranged above a base 55 adapted to enclose certain operating parts, as will further appear, this base desirably being substantially completely enclosed, except for certain ports or passages through which connections extend, as will be described. Below the bottom wall of the base or enclosure 55 means for supporting the unit are provided, preferably including a pair of laterally spaced wheels 56, and a pair of downwardly projecting spaced side wall elements 57, which may conveniently take the form of triangular pieces, with one corner of each presented downwardly to provide for support as on the floor indicated at F in FIG. 7.

With the equipment arranged in the general manner described above, the various components are conveniently arranged and assembled in an overall structure which may readily be wheeled from place to place and which will also stand in a stable upright position because of the supporting elements 56 and 57.

With regard to the general arrangement it is further to be observed that superimposed above the top wall 51 of the vacuum chamber a control box is provided as indicated at 58, this box having a top wall or panel 59 with which various of the operating controls are associated, especially those which are located within the control box 58.

The inclined front wall 54 is preferably hinged along its lower edge as indicated at 60 so that this wall serves as a displaceable closure movable between the full line closed position shown in FIG. 7 at 54 and the dotdash open position 54a. Straps 61 each having a slot cooperating with a pin are provided to limit the opening movement of the front wall in the manner plainly shown in FIG. 7. The wall 54 may be fastened in closed position by means of a pivoted latch device 62 cooperating with a keeper 63.

Opening the front panel provides for ready access to the suction bag 16, which is conveniently hung from hooks 64 depending from the top wall 51 of the vacuum chamber. The bag is desirably of the construction described above, having a suction tube 15 and also a drain 22 with cap 23 constructed as described. Along the edge of one of the side walls 53, a notch 14 is provided to accommodate the suction tube 15, in a manner very similar to the arrangement shown in the first embodiment. It will be understood that sealing gaskets or other sealing elements will be employed to avoid leakage and loss of vacuum, for instance along the meeting edges of the displaceable wall 54 and the side, top and bottom walls of the chamber, as well as in the region of the notch 14 for accommodation of the suction tube 15.

In the bottom portion of the suction chamber an upright wall 65 is provided, projecting upwardly from the bottom wall 52 and extending laterally between the side walls 53, this wall 65, cooperating with other wall elements of the vacuum chamber to define a sump which will receive and retain liquids, in the event of inadvertent spillage or leakage, for instance because of a damaged suction bag. Preferably the wall 65 is of sufficient vertical height so that the pump provided has a volumetric capacity at least as great as the normal charge in one of the suction bags. It will also be noted that the vacuum connection 24 which extends upwardly through the bottom wall of the vacuum chamber extends to a height somewhat above the upper edge of the wall 65, so that even in the event of accumulation of liquid in the sump, this liquid will not enter the vacuum system.

It is contemplated that the equipment shown in FIGS. 7–10 be capable of operation either by the action of a selfcontained aspirator comprising the suction pump 26 and motor 27, or by an externally available vacuum source which may be coupled with the equipment by means of the plug-in vacuum connection 33 of the kind above described, cooperating with the connector 32. These two sources of vacuum are respectively controlled by normally closed solenoid operated valves 30 and 31 as in the first embodiment, both of these valves being associated with the vacuum connection 24 which is extended from the base enclosure upwardly into the vacuum chamber. Preferably the base enclosure 55 is provided with an opening with which a filter device 66 is associated, desirably in the form of a replaceable filter unit, so that any discharge through the opening from the interior of the base enclosure from the suction pump 26 will be filtered before discharge into the surrounding air.

Figure 10:
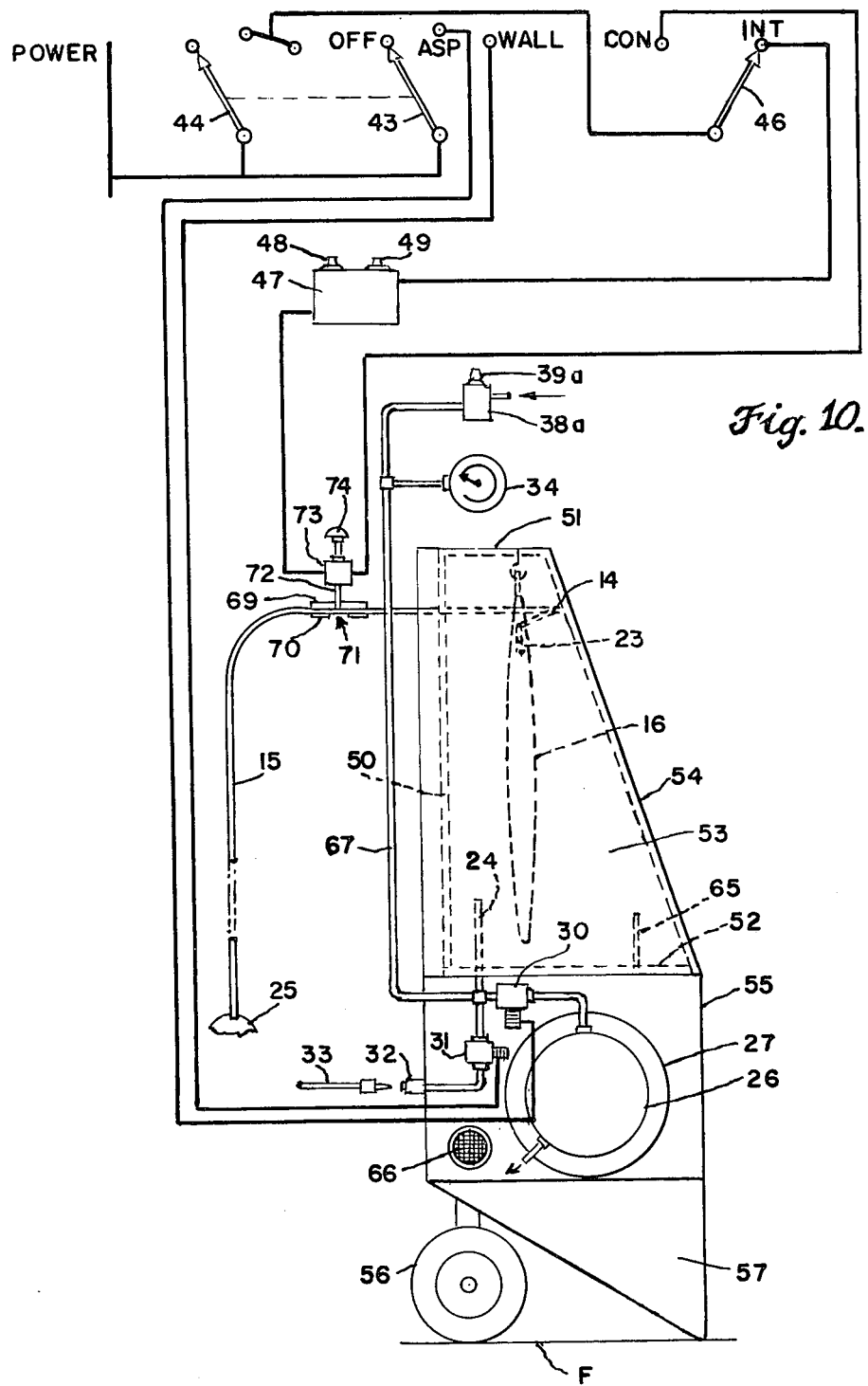
FIG. 10 is a schematic view of the fluid pressure and other controls employed with the equipment of FIGS. 7, 8 and 9.

The arrangement of the controls appears to best advantage in the schematic view of FIG. 10. Here it will be seen that the vacuum connection 24 which communicates with the intake sides of the solenoid valves 30 and 31, also communicates with a connection 67 which extends from the base enclosure upwardly at the back of the vacuum chamber, for instance through an enclosed duct or channel 68 (see especially FIG. 7), this connection 67 being associated with controls arranged in the control box 58 at the top of the unit, as described below with particular reference to the schematic view of FIG. 10.

A pressure gauge 34 is associated with the vacuum line 67, and in addition an adjustable bleed valve 38a, having an adjustable control knob 39a is associated with the vacuum connection 67, these devices (34 and 39a) being mounted on the panel 59 at the top of the control box, as will be seen from FIG. 8. The timer device 47 is also located in this control box and the two control knobs 48 and 49 of this timer are positioned above the panel 59 as also appears in FIG. 8.

The timer mechanism in the embodiment of FIG. 7 is arranged to operate in a somewhat different manner than in the embodiment of FIGS. 1–6. Thus, whereas in FIGS. 1–6 the timer mechanism operates on the suction side of the system, i.e., operates on the vacuum connection 24 by means of which the vacuum is developed in the vacuum chamber, in the embodiment of FIGS. 7–10 the timer mechanism is arranged to operate on the suction tube 15 which, in effect, is the pressure side of the system, i.e., the side at which atmospheric pressure is acting to cause flow of the liquids through the tube 15 into the suction bag. Outside of the vacuum chamber, at one side wall thereof, a bracket 69 is provided, the lower edge of this bracket having an upwardly open channel 70 adapted to receive the tube 15. When a bag is inserted in the vacuum chamber and the tube introduced into the notch 14, the tube may also be manually laid into the channel 70 and then extended to the source 25 of the liquid to be drawn into the suction bag. The midportion of the channel 70 is cut away as indicated at 71 in FIG. 9, in a position below the plunger 72 of the solenoid device 73. The solenoid device is of the type in which the plunger 72 is biased downwardly, as by spring pressure, and when the plunger is pressed downwardly against a tube 15 in the channel 70, the tube will be closed by being deflected into the recess 71. The plunger 72 may be manually lifted by the handle 74 provided at the top of the solenoid device. The plunger 72 may also be raised by action of the solenoid under the influence of the timer 47, in which event the raising of the plunger will be intermittent, the control knobs 48 and 49 providing for control of the period during which the plunger is raised and also for control of the interval between periods when the plunger is raised.

The solenoid 73 may be activated constantly, thus maintaining the plunger 72 in raised position at anytime the switch 46 is positioned in the CON position.

As in the first embodiment, the arrangement of FIGS. 7–10 includes a control knob 45 for the switch providing for alternative intermittent or constant operation (see FIG. 8.) In addition switch buttons 43a, 43b and 43c are provided on the control panel as shown in FIG. 8, these buttons serving to operate the switch parts indicated at 43 and 44 in FIG. 10 and serving respectively to establish the OFF, ASP and WALL conditions.

The arrangement of the solenoid 73 as described hereinabove, has a number of distinctive advantages including the fact that at anytime when the system is completely turned off, as by pushing the OFF button, the plunger 72 will close the tube 15, which is desirable in order to prevent gravity flow of liquid in reverse direction through the tube 15 to the body cavity from which liquids have been withdrawn.

When the equipment is being operated with the switch 46 in the CON position the plunger 72 will be lifted so that fluids may be drawn through the tube 15 into the suction bag 16. When the switch 46 is in the INT position the plunger 72 will be intermittently raised and lowered, thereby intermittently opening and closing the suction tube 15. This provides an intermittent suction operation without changing the vacuum or pressure reduction in the vacuum chamber and the suction bag. This provides for intermittent operation without involving any time delays for pressure reduction or pressure increase in the vacuum chamber. The positioning of the tube 15 in the channel 70 is a simple and readily effected operation, merely requiring manual lifting of the spring pressed plunger 72 by the handle 74, in order to raise the plunger to a position above that established by the solenoid and its return spring, so that the tube may readily be placed in the channel 70 below the plunger 72. Upon release of the handle the plunger will descend under the action of the return spring to close the tube, unless the equipment is in operation, in which event the plunger will be kept by the control circuits in the position shown in which the tube is open.

Turning now to the embodiment of the equipment as illustrated in FIGS. 11 to 17, it is first to be understood that although not all parts of the equipment are shown in these figures, the parts which are not illustrated may be of the kind disclosed above, especially in the second embodiment which is shown in FIGS. 7 to 10, but the equipment of the third embodiment incorporates certain differences as compared with the equipment of the second embodiment as will be pointed out.

It is also to be understood that certain of the features described herebelow in connection with the third embodiment may also be used in the first or second embodiments, for instance the phases of the control system providing for automatic transfer of operation from the self-contained suction source to an external suction source, and also the sealing means for the suction tube, as particularly described with reference to FIGS. 13 to 17.

Still further it is to be understood that bags and suction tubes of the kind described above are contemplated for use also in the third embodiment, although the sealing means for the suction tube employed in the third embodiment embodies differences from what has been described with reference to FIGS. 1 and 2, as will further appear.

Turning now to the system as diagramed in FIG. 11, it will be noted that the vacuum chamber of this embodiment is of the kind shown in FIGS. 7 and 10, but in FIG. 11 the mounting of various of the control parts in the base has not been illustrated as this portion of the equipment may be arranged in the same manner as the third embodiment. The bag in the suction compartment is again indicated at 16 and it is contemplated that this may be the same kind of bag described above, having provision for communication between the interior of the bag and the interior of the chamber as illustrated in FIG. 6 and having a suction tube which is here indicated at 15a, having certain differences from the tube 15 of the first two embodiments, as will be explained hereinafter.

The vacuum system or the vacuum chamber includes the principal vacuum connection 24, of the kind described above, associated with a different form of control system as is illustrated in FIG. 11 and described below.

It is first noted that the pressure gauge 34 is here shown as being directly connected with the vacuum chamber separately for the connection 24, although it will be understood that the pressure gauge may alternatively be connected with the vacuum connection 24.

The self-contained source of suction, namely the motor 27 and the pump 26, is provided and this pump is connectable with the vacuum connection 24 through the solenoid valve 30 which is a normally closed valve, as in the other embodiment. The discharge of the pump 26 may be delivered through a filter 66, in the manner previously described in reference to FIG. 7.

Connections 67a extend from the main suction line 24 to the adjustable bleed valve 38a, by means of which air may be bled into the system, thereby limiting the maximum suction, in the manner previously described. This device is adjustable by means of the nob 39a. In the embodiment of FIG. 11, a branch connection 74 is also provided and is provided with a petcock or other quick release valve indicated at 75 which may be opened to rapidly dissipate the suction in the system should that be desired at any time, for instance, just prior to opening of the closure 54 of the vacuum chamber in preparation for removing a suction bag.

Another branch 76 of the suction system extends to the bleed valve 77 which is adjustable by the nob 78 and this line also includes the normally closed solenoid valve 79 adapted to be opened and closed by the timer 47 having controls 48 and 49, as above described, for regulating the intermittent operation, both with respect to the length of the suction periods and also the intervals between the intermittent suction periods.

In this system for intermittent operation, the adjustable valve 77 may be used to establish and control the minimum suction level. In this way, in combination with the device 38a, both the maximum and minimum suction levels may be adjusted independently. When the timer 47 permits the valve 79 to close, then the suction level is established by the valve 38a, and when the timer operates to open the valve 79 the adjustable valve 77 will permit additional air to bleed into the system. The valve 77 may be adjusted so that even when the valve 79 is open, there will still remain a low level of suction in the system.

The provision of intermittent operation as just described provides an effective way of preventing backflow in the suction tube of the bag during the timed intervals of "rest". This operation at timed alternate intervals of higher and lower suction is advantageous under certain conditions and use of the equipment, as it not only prevents backflow during the rest periods, but also provides for resting of the tissues and wound, and still further for dislodgement of any clot or material tending to accumulate and block the drainage system.

If it is desired to have no suction in the rest intervals, this may also be achieved by adjusting the valve 77 to its maximum opening, in which it is contemplated that sufficient air will bleed into the system through the branch connection 76 to completely dissipate the vacuum during the rest periods.

Still another branch 80 of the suction system is provided with two normally open solenoid operating valves 81 and 82 which are arranged in series, the line 80 ultimately terminating in a connector 32 and serving the same purpose as connector 32 above described in connection with the first and second embodiments. Thus, this connector is adapted to be coupled with the connector 28 of a wall vacuum outlet, a disconnectable tube 33 being provide for that purpose as in the earlier embodiments. This system provides for alternative operation of the equipment on the external source of suction instead of on the internal suction pump.

All of the elements in the system as described above in reference with FIG. 11, are adapted to be controlled by an electrical system diagrammatically indicated in FIG. 11 and here shown as including an ON/OFF push button switch 83 in the power line P. When the power switch 83 is in the ON position it provides for delivery of current to the three control switches indicated as push buttons 84, 85 and 86 (see also FIG. 12). When the push button 84 which is labeled PUMP is actuated, the motor 27 of the self-contained suction system is activated and in addition the solenoid valve 30 is opened, thereby providing for operation of the equipment on the self-contained suction source. At the same time, it will be seen that this circuit delivers current to the normally open solenoid valve 81 thereby closing that valve, so that the vacuum connection 80 is closed off. With the WALL STOP push button switch 86 operated, current is also delivered to the normally open solenoid valve 82 thereby closing that valve. The provision of the two normally open valves 81 and 82 thus provides for alternative operation either on the internal suction source or on the external suction source, and in addition this arrangement provides a safety factor which may be explained as follows:

Assuming the equipment is in operation on the self-contained suction source, it is only effective when electric power is available. If the electric power should fail (for instance by the opening of a circuit breaker or fuse), the failure of the power will, of course, result in termination of the operation of the self-contained suction source, but at the same time, the loss of current will result in opening of both of the normally open valves 81 and 82 and assuming the connection 33 has been made to the external source of suction, the operation of the equipment will automatically be diverted to and will continue operation on the external source of suction. On the other hand, even when power is available, the operation of the push button switches 84 and 86 will provide for selective operation either on the self-contained suction source or upon the external source, and when operating on the external source, the operation of the push button switch 86 may be used to either open or close the valve 82, which may from time to time be desired.

Since the solenoid valve 79 is a normally closed valve, the intermittent operation will only be operative when power is available. The intermittent functioning of the equipment may, of course, be controlled by the INT switch button 85 operated either to activate or deactivate the timer 47.

In considering the third embodiment, some features of the control panel as shown in FIG. 12 should be noted.

In the first place, it will be understood that the control panel may also be mounted on top of the vacuum chamber as indicated at FIG. 7. FIG. 12 shows a suitable disposition for the switches 83, 84, 85 and 86 and it may be observed in connection with those switches that they may each comprise a push button type of switch in which successive actuations of the push button results in successive connection and disconnection of the circuit. Desirably these push button switches contain signal lights and are color coded so that a glance at the control panel will inform the operator of the condition of the controls.

From FIG. 12, it will also be seen that the quick suction release petcock 75 is shown on the control panel, as is also the suction gauge 34 and the two adjustable control valves 38a and 78 which are provided respectively for regulating the high suction level and the low suction level, as described above. With regard to the low suction level, if desired, this adjustable valve may be interiorly disposed in the equipment so as not to be readily accessible to operating personnel and may even be a valve having a fixed setting, but for some purposes, it is advantageous to have this low suction level adjustment accessible on the control panel for use by the operating personnel.

It will also be noted that the illustration of the control panel in FIG. 12 does not indicate the adjustable controls 48 and 49 for the timer 47, and it is here contemplated that this timer and its controls may also be located interiorly of the equipment so as to require pre-setting, rather than normal adjustment by the operating personnel. On the other hand, if desired, the timer controls may be mounted on the control panel as is the case on the second embodiment described above and shown in FIG. 8.

Turning now to the feature illustrated in FIGS. 13 to 17, it is first noted that a suction tube for a bag is indicated by the reference numerial 15a. From the enlarged fragmentary view of FIG. 13, it will be seen that the edge of the side wall 53 of the suction chamber is provided with two tube receiving notches or recesses 87 and 88. This has been done so that more than one bag each with a separate suction tube, may be mounted in the vacuum chamber, the equipment being capable of handling more than one bag, so that if required for some special purposes, liquids may be withdrawn separately from more than one source. Because of the vacuum or suction condition within the chamber, it is of course important to provide a substantially leak proof seal around the tube at the point where the tube passes through the wall of the chamber from the bag to the intake catheter. In the embodiment illustrated in FIGS. 13 to 17, each notch or recess such as indicated at 87 is desirably of larger size than the tube to be received, and a sealing device or adaptor is applied to the tube and seated in the notch 87. Advantageously the sealing device comprises an adaptor 89 formed of soft or resilient material, for instance, expanded or porus sponge type plastic such as polyvinyl chloride resin material. Alternatively, sponge or soft rubber may be used. As seen in FIG. 13, at each side of the adaptor 89 extended wings 89a are provided, and the notch in the side wall 53 desirably includes portions recessed to accommodate the wings 89a. Moreover the device 89 is also desirably provided with flanges indicated at 89b forming a channel structure embracing the side wall 53.

The sealing device 89 may completely surround the suction tube 15a, in which case it would be necessary to apply the sealing device to the tube by sliding it over one end of the tube and along the tube to the desired position. Alternatively, the sealing device may be slit at the side facing the closure 54, so that the device may be applied to the tube transversely.

It is contemplated that the sealing device snuggly fit the engaged surfaces of the side wall 53 of the vacuum chamber and also the adjacent flat surface of the closure door 54. Ordinarily, the suction tube itself is also formed of a soft or pliable plastic material, and by employing a sealing device of the kind described above, upon such a plastic tube, the sealing device may readily be proportioned so that the material thereof is placed under slight compression when the door 54 is closed, thereby assuring a leak proof joint where the tube passes out of the vacuum chamber.

The sealing device may constitute a separately handleable adaptor, as shown in FIG. 17, which may be applied to the suction tube at the time the bag and the tube are being inserted in the equipment for use. On the other hand, the sealing device may advantageously be adhesively secured or permanently bonded to a suction tube which is either intergral with or which may be assembled with a suction bag. It is desirable to have the sealing device permanently fastened to the tube regardless of whether the tube is permanently fastened to the bag or comprises a separate component to be assembled with a bag. This has a special advantage which is explained as follows:

Various bags and associated suction tubes may be used in the equipment of the invention, the tubes being of different diameter. To insure a tight seal with tubes of different diameters, it is important that the sealing device have different dimensions corresponding to the individual dimensions of the tube being used. If the sealing device comprises a separate adaptor, there would necessarily have to be sealing devices of different sizes maintained in stock in order to have adaptors available for tubes of different sizes. However, if a properly proportioned sealing device is permanently fastened to each suction tube, errors in assembly are avoided. In all cases, of course, the external dimensions of the sealing devices are appropriate to the size of the notch in the edge of the chamber wall 53. Thus, by providing a sealing device permanently fastened or assembled with each tube, whether or not the tube is permanently assembled with a bag, a snug seal is assured, and therefore maintenance of the desired suction condition is also assured.

In the case of the presence of a notch such as indicated at 88 in FIG. 13 which at times is not being used for a suction tube, that notch may be closed be means of a "blank" adaptor as indicated at 90, this adaptor having flanges 90b as indicated to embrace the edge of the side wall 53 and to provide for complete enclosure of that notch when it is not being used for a suction tube.

In all three embodiments, the use of the vacuum system to produce the suction in the suction bag is advantageous from a number of standpoints including the fact that this system facilitates the employment of disposable suction bag and suction tube components. It will be observed that no part of the disposable components need be introduced into any mechanical pump device. Moreover, the system of the present invention is capable of establishing and maintaining a given suction condition immediately from outset of operation, and this condition will be maintained at the selected suction or pressure level without variation, regardless of fluctuations of the quantity of liquid in the suction tube or in the suction bag.

The equipment is simple, inexpensive and reliable and presents virtually no hazards from the standpoint of contamination of the non-disposable portions of the apparatus.

The embodiments of FIGS. 7-10 and of FIGS. 11-17 are also very flexible and adaptable to use under a variety of conditions and in a variety of positions, since the equipment may readily be wheeled from place to place. The arrangement of the vacuum chamber in the embodiments of FIGS. 7-10 and 11-17, with the pivotally mounted door or closure 54 also provides maximum convenience in introducing and removing the suction bags.

I claim:

1. Equipment for withdrawing body liquids comprising a vacuum chamber, a suction bag adapted to be removably positioned in the vacuum chamber and having an opening for interconnecting the interior of the bag with the interior of the chamber, the bag further having an inlet connection comprising an inlet tube with the tube wall connected with the wall of the bag and extended therefrom to a point exterior of the vacuum chamber for intake of body liquid, a vacuum line adapted to be connected with a pressure reduction source of substantially constant reduced pressure, said line being connected with the vacuum chamber independently of the bag and being in communication with the interior of the vacuum chamber externally of the bag, and mechanism providing for timed intermittent fluctuation of the suction in said chamber between upper and lower negative pressure limits.

2. Equipment as defined in claim 1 and further including means for adjustably varying at least the lower limit of the suction fluctuation.

3. Equipment as defined in claim 1 and further including means providing for separate adjustment of both the upper and lower limits of the suction fluctuation.

4. Equipment for withdrawing body liquids comprising a chamber having an imperforate wall structure and a displaceable closure member cooperating to define a closed but openable vacuum compartment for receiving a disposable suction bag having a liquid inlet tube, means for mounting such a bag in the vacuum compartment, a suction line communicating with the vacuum compartment, means for controlling the suction communicated to the vacuum compartment, timer mechanism for intermittently fluctuating the suction between a relatively high suction value and a relatively low suction value, and means for variably adjusting said relatively low suction value.

5. Equipment as defined in claim 4 and further including means for variably adjusting the relatively high suction value of the timed fluctuation.

6. Equipment for withdrawing body liquids comprising a chamber having an imperforate wall structure and a displaceable door cooperating to define a closed but openable vacuum compartment adapted to receive a suction bag having a liquid inlet tube for intake of body liquid, a vacuum line communicating with the vacuum compartment, the equipment incorporating a self contained suction source, first valve means providing for connection of said vacuum line with said self contained suction source, second valve means providing for alternative connection of said vacuum line with an external suction source, the first valve means being normally closed and the second valve means being normally open, and control means operating to close the second valve means when the first valve means is opened.

7. Equipment as defined in claim 6 in which the first valve means is power operated to effect opening thereof and in which the second valve means is power operated to effect closing thereof, thereby providing for opening of the second valve means and closing of the first valve means upon power failure.

8. Equipment as defined in claim 7 and further including third valve means in series with said second valve means, the third valve means being normally open and being power operated to effect closing thereof, and manually operable power control for the third valve means.

9. Equipment for withdrawing body liquids comprising a chamber having an imperforate wall structure and a displaceable door cooperating to define a closed but openable vacuum compartment for receiving a disposable suction bag having a liquid inlet tube, said wall structure and said door having portions cooperating to form a channel therebetween which is laterally open when the door is open and thereby provide for transverse insertion and removal of the inlet tube of a bag, and a pressure sealing device fitting said channel and proportioned to have pressure sealing engagement with the inlet tube of a bag received in the vacuum compartment, the sealing device being in the form of a replaceable adapter to thereby provide for accommodation of bag inlet tubes of different sizes.

10. Equipment for withdrawing body liquids comprising a chamber having an imperforate wall structure and a displaceable door cooperating to define a closed but openable vacuum compartment for receiving one or more suction bags each having a liquid inlet tube, said wall structure and said closure having portions cooperating to form a plurality of channels therebetween each of which is laterally open when the door is open and thereby provide for transverse insertion and removal of the inlet tubes of bags, and means for closing any unused channel thereby providing for operation of the equipment alternatively with one or more bags.

11. A disposable suction bag with an inlet tube for use in a vacuum chamber having an imperforate wall and a removable closure with cooperating portions forming a tube receiving channel therebetween, the inlet tube of the bag being connected with the upper portion thereof and having a pressure sealing device secured thereto in position to engage said cooperating portions of the wall and closure of the vacuum chamber, and the sealing device being formed of resilient material and being proportioned to be placed in compression in said channel when the removable closure is closed and thereby provide a pressure seal in the tube receiving channel, the bag further having an outlet connection in the form of an open ended tube connected with the upper portion of the bag to provide for communication of the interior of the bag with the vacuum chamber when the bag is inserted therein, and a cap over the open end of the outlet tube having portions providing a leakage groove therebetween providing for communication of the interior of the bag with the vacuum chamber into which the bag is inserted, even when the cap is applied to the open end of the outlet tube.

12. Equipment for withdrawing body liquids comprising a chamber having an imperforate wall structure and a displaceable door cooperating to define a closed but openable vacuum compartment adapted to receive a suction bag having a liquid inlet tube for intake of body liquid, the equipment further comprising a cabinet structurally connected with the vacuum chamber, and operating and control mechanism in said cabinet including a self contained suction source having an outlet arranged to discharge externally of said cabinet, a replaceable filter in said discharge outlet, a vacuum line extended from said cabinet and communicating with the vacuum compartment, first valve means providing for connection of said vacuum line with said self contained suction source, second valve means providing for alternative connection of said vacuum line with an external suction source, the first valve means being normally closed and the second valve means being normally open, and control means operating to close the second valve means when the first valve means is opened.

* * * * *